United States Patent [19]

Kötzsch et al.

[11] 4,039,567
[45] Aug. 2, 1977

[54] PROCESS FOR THE CONTINUOUS ESTERIFICATION OF CHLOROSILANES

[75] Inventors: Hans-Joachim Kötzsch, Rheinfelden; Hans-Joachim Vahlensieck, Wehr, Baden, both of Germany

[73] Assignee: Dynamit Nobel Aktiengesellschaft, Troisdorf, Germany

[21] Appl. No.: 584,271

[22] Filed: June 5, 1975

[30] Foreign Application Priority Data

June 5, 1974 Germany .............................. 2427085

[51] Int. Cl.² ............................ C07F 7/04; C07F 7/18
[52] U.S. Cl. ....................... 260/448.8 R; 260/448.8 A
[58] Field of Search ................... 260/448.8 R, 448.8 A

[56] References Cited

U.S. PATENT DOCUMENTS

| 3,792,071 | 2/1974 | Nitzsche et al. .............. 260/448.8 R |
| 3,801,618 | 4/1974 | Walker ...................... 260/448.8 R X |

*Primary Examiner*—Paul F. Shaver
*Attorney, Agent, or Firm*—Burgess, Dinklage & Sprung

[57] ABSTRACT

An improvement in a process for the preparation of an alkoxysilane of the formula:

$$R_{4-n-m}Si(OR')_nCl_m$$

wherein
R is hydrogen or a saturated or unsaturated, chlorinated or unchlorinated alkyl radical of 1 to 12 carbon atoms;
R' is an alkyl radical of 1 to 11 carbon atoms which can contain a hetero atom in the chain;
$m$ equals 0 to 3;
$n$ equals 1 to 4;
$n + M$ is equal to or less than 4;
by esterification of a chlorosilane of the formula:

$$R_{4-n}SiCl_n$$

wherein R and $n$ have the previously assigned significance with an alcohol, the improvement residing in continuously charging liquid alcohol and liquid chlorosilane from a separate source into a distillative reaction zone having a head portion and a sump portion, maintaining the head portion at a temperature sufficient for said esterification, continuously distilling off gaseous HCl formed during said esterification while maintaining the resultant reaction mixture in the sump at its boiling point and continuously separating liquid alkoxysilane from the sump.

7 Claims, No Drawings

PROCESS FOR THE CONTINUOUS ESTERIFICATION OF CHLOROSILANES

BACKGROUND OF THE INVENTION

1. Field of the Invention

This invention relates to the preparation of an alkoxysilane. More particularly, this invention relates to a continuous process for the production of alkoxysilane wherein HCl gas is continuously removed from the reaction mixture in a distillative reaction zone while the resultant reaction mixture is maintained at its boiling point and liquid alkoxysilane is removed from the sump portion of the distillative reaction zone. This invention is particularly directed to a continuous process for the production of alkoxysilane where alkoxysilane is obtained in substantially quantitative amounts in liquid form.

2. Discussion of the Prior Art

The esterification of chlorosilanes is performed in accordance with the following equation when $SiHCl_3$ is the chlorosilane:

$$HSiCl_3 + n\, R'OH \rightarrow HSi(OR')_nCl_{3-n} + n\, HCl$$

In this equation, R' represents an alkyl radical of 1 to 11 carbon atoms, and $n$ can assume values between 1 and 3.

The practical performance of this reaction, and of analogous reactions in which a saturated or unsaturated alkyl group replaces a hydrogen atom, causes difficulties because the hydrogen chloride that forms in large quantity in that case, not only cleaves the alkoxy group to alcohol and chlorosilane but also, particularly in the presence of alkanol, cleaves the hydrogen silane compound thereby yielding hydrogen and forming an alkoxysilane compound and a chlorosilane compound. In addition, the hydrogen chloride, in turn, forms chloroalkanes from alkanols charged. Intermediately there is formed water which, in turn, attacks the chlorosilanes and alkoxysilanes. Unless certain process conditions are maintained, the desired silane ester is usually completely lost due to this secondary reaction.

Consequently, a number of attempts have been made to produce such compounds in a more economical manner. The low rate of formation of the condensate, which encumbered the original batch process and was due to the above-described secondary reactions of the hydrogen chloride with the alcohols used for the esterification, can be largely eliminated by the use of modern batch procedures. However, there are limits to the application of such procedures to large-scale technical production, especially on account of the difficulty of controlling the large quantities of hydrogen chloride in conjunction with sometimes low-boiling starting substances, and the large and steep temperature gradients required both in the reaction chamber and in the exhaust for the safe control of the reaction. A continuous process is therefore to be preferred, if only for reasons of better temperature control.

Thus, continuous processes have already been proposed in which chlorosilanes, in the presence of solvents in some cases, are esterified in the liquid phase, either in a reactor provided with an overflow, borrowed from the simplest batch process, or in a plurality of reactors joined together in series on the basis of the counterflow system. This process, however, has the disadvantage that the hydrogen chloride is removed too slowly and incompletely. This results in the cleavage of ester groups already present and in secondary reactions between the alcohols and the hydrogen chloride with the formation of undesirable hydrolyzates. Another prescribed method involves the esterification of chlorosilanes with alcohols in the gas phase. This method uses temperatures which are above the boiling points of all the substances, i.e., reactants as well as end products.

The latter process, however, has a particularly great disadvantage because the hydrogen chloride present in the system coupled with the elevated temperature employed produces the known secondary reactions at a particularly great speed, especially reverse cleavage, alcohol dehydration and the formation of hydrolyzates.

The special weakness of all the continuous esterification processes described above is the excessively slow and incomplete separation of the hydrogen chloride from the reaction mixture. It has already been proposed, therefore, to blow out the hydrogen chloride by passing inert gases, nitrogen for example, over or through the mixture, in some cases with the aid of a falling film evaporator, in which case an upper temperature limit may not be exceeded. This procedure, however, again has the considerable disadvantage that the volume of the exhaust gas consisting of hydrogen chloride is increased. This makes the evaporation losses due to the partial pressure of the products unacceptably high. The reuse of the hydrogen chloride under such circumstances is therefore virtually impossible. On the other hand, the inert gas treatment does not accomplish a complete separation of the hydrogen chloride from the raw product.

It has therefore become desirable to provide a process for the continuous esterification of chlorosilanes with alcohols wherein hydrogen chloride removal is virtually complete and liquid alkoxysilane is obtained having a low concentration of HCl. It has become particularly desirable to provide a process which yields quantitative amounts of alkoxysilane by esterification of chlorosilanes with alcohol. It is an object of this invention, therefore, to provide such a process.

SUMMARY OF THE INVENTION

In accordance with this invention there is provided an improved process for the preparation of an alkoxysilane of the formula:

$$R_{4-n-m}Si(OR')_nCl_m$$

wherein
R is hydrogen or a saturated or unsaturated, chlorinated or unchlorinated alkyl radical of 1 to 12 carbon atoms;
R' is an alkyl radical of 1 to 11 carbon atoms which can contain a hetero atom in the chain;
$m$ equals 0 to 3;
$n$ equals 1 to 4;
$n + m$ is equal to less than 4;
by esterification of a chlorosilane of the formula:

$$R_{4-n}SiCl_n$$

wherein R and $n$ have the previously assigned significance with an alcohol, the improvement residing in continuously charging liquid alcohol and liquid chlorosilane from separate sources into a distillative reaction zone having a head portion and a sump portion, maintaing the head portion at a temperature sufficient for said esterification, continuously distilling off gaseous HCl formed during said esterification while maintaining the resultant reaction mixture in the sump at its boiling point and continuously separating liquid alkoxysilane from the sump.

It has surprisingly been discovered that the distillative reaction procedure of the present invention yields substantially quantitative amounts of liquid alkoxysilane. Moreover, the amount of HCl recovered overhead from the distillative reaction zone is obtained in quantitative amounts. Thus, not only is the HCl virtually completely removed overhead so that no side reactions can be accomplished but there is also obtained quantitative amounts of alkoxysilane. Thus the HCl is prevented from effecting secondary reactions to any significant extent. Yields of well better than 90%, based upon the amount of chlorosilane charged are readily obtained. Thus the difficulties outlined above are obviated by the present process wherein the HCl that forms is removed continuously and completely by distillation without any appreciable competing or secondary reactions.

It has been surprisingly found that if the reaction mixture is maintained at a temperature under the prevailing pressure that is sufficient for the HCl formed to be distilled off that quantitative yields of alkoxysilane are obtained. This is considered quite surprising since it was believed by those of skill in the art that the maintenance of these elevated temperatures in a column distillation vessel would favor the undesirable secondary reactions which compete with the primary reaction and significantly reduce the yield of alkoxysilane. The realization of quantitative yields of alkoxysilane could not have been predicted from the state of the chlorosilane esterification art as described in the various literature references. However, it has been surprisingly found that by the process of the present invention virtually quantitative yields of a wide variety of silane esters of great purity are obtained in a most elegant manner. Additional advantages obtained by the present invention include:

A. A quantitative separation of hydrogen chloride in sufficient purity that it is suitable for reuse; and B. An uncomplicated adaptability of the described process to large-scale production.

The process of the present invention begins with the utilization of liquid reactants. The liquid alcohol and the liquid chlorosilane are introduced to the distillation reaction zone from separate sources; i.e., they are not pre-mixed. The reactants are preferably introduced into a distillative reaction zone provided with a head portion and a sump portion. To the head portion there is fixed a condenser for condensing the HCl removed from the distillative reaction zone so that it can be readily recovered. Within the distillative reaction zone itself it is preferred that there be a suitable number of horizontally disposed trays. The esterification reaction, which usually starts spontaneously when the two reactants are combined, takes place, insofar as possible, on the topmost spreader tray of the column. Small quantities of reactants are allowed to descend to lower spreader trays to complete the reaction. However, the liquid reactants are not permitted to descent more than about 15% of the height of the distillation column.

The amount of alcohol and chlorosilane employed is governed according to the desired end product. Consequently, stoichiometric amounts corresponding to the desired degree of esterification are fed simultaneously into the topmost tray of the column. Slight departures from this stiochiometric molar ratio can be tolerated in accordance with the invention, although they do diminish yields. For this reason, such departures should not be greater than a tolerance of about ±1%.

The reactants are introduced onto the topmost spreader in liquid form. In such form they react with one another with evolution of HCl gas. Solvents can be employed for the reaction, particularly when the desired silane ester has a boiling point above about 180° C. The solvent in this gas can be admixed with either starting substance or it can be introduced from a separate or third line. The solvent is also introduced onto the topmost spreader tray of the distillation column.

The use of solvents serves mainly to permit the process of the invention to be performed so as to produce those silane esters whose boiling points are above the range of 0° to 180° C, or which decompose at their boiling point. Thus the process can be carried out such that the desired silane ester is kept boiling at a desired temperature under normal conditions, at the boiling point of its mixture with the solvent and thus to obviate the necessity of employment of a vacuum.

In the method of the invention, solvents are preferably not used when the desired silane ester boils at normal pressure between 0° and 180° C, as is the case, for example, when trichlorosilane or tetrachlorosilane are esterified with low alcohols having one or two carbon atoms. If, however, these silanes are reacted with higher alcohols, such as 2-methoxyethanol, for example, the addition of a suitable solvent gives the advantage that the esterification process of the invention can be performed at normal pressure even though the pure end product is not distillable at normal pressure. Preferred solvents for this purposes are chlorinated hydrocarbons, especially the dichlorethylenes and trichlorethylene, but also mono-, di-, tri- and tetrachlormethane, for example, for various fluorochlorinated hydrocarbons.

DESCRIPTION OF THE SPECIFIC EMBODIMENTS

Basically any known distillation column is suitable, the trays also being of known types, such as bubble trays for example. The column is preferably packed with known packing bodies, such as ceramic saddles, rings or balls, for example. The number of trays is also widely variable; about 25 to 35 trays are preferred.

After the end of the reaction, the desired silane ester flows into the body of the still where it is maintained at the boiling temperature. Depending on the input of heat to the still and on the nature of the starting substances, of the esterification product and of the solvent is any, a temperature between about 0° and 90° C will establish itself in the upper portion of the column where the reaction is taking place. In the meantime, the hydrogen chloride forming in the reaction is distilled completely away. It is completely condensed in a condenser maintained at temperatures between about $-10°$ C and $-80°$ C which is connected to the top of the distillation column, and it is reserved for further use.

The silane ester obtained by the present method flows continuously from the still overflow in a purity which is already sufficient for most applications. It can be separated from any solvent that may be present by distillation or by other known separating processes.

The preferred starting substances as far as the chlorosilanes are concerned are trichlorosilane, tetrachlorosilane, methyldichlorosilane, dimethyldichlorosilane, trimethylchlorosilane, methyltrichlorosilane, ethyltrichlorosilane, vinyltrichlorosilane, propyltrichlorosilane, allyltrichlorosilane, 3-chloropropyltrichlorosilane, n- and isobutyltrichlorosilane. Alkylchlorosilanes having a higher straight-chained or branched alkyl radical are also usable.

Suitable alcohols are, for example, methanol, ethanol, propanol, butanol, octanol, 2-methoxyethanol, 2-ethoxyethanol, 2-methoxyethyldiethyleneglycol ether, tetrahyrofurfuryl alcohol, etc.

The following products can be obtained, for example, by the method of the invention: trimethoxysilane, triethoxysilane, tetraethoxysilane, tri-2-methoxyethoxysilane, tetra-2-methoxyethoxysilane, methyldimethoxysilane, methyldiethoxysilane, vinylmethyldiethoxysilane, methyltriethoxysilane, vinyltriethoxysilane, vinyltri-2-methoxyethoxysilane, 3-chloropropyltriethoxysilane.

A number of the ester compounds of silicon referred to above are achieving increasing technical importance. For example, a number of silicic acid ortho esters are being used as binders for zinc dust colors and in foundry operations. Several organosilane esters are used as structure protecting agents. Some other organosilane esters are gaining technical importance in the synthesis of very valuable organofunctional silanes. Hydrogen silane esters are also of interest in semiconductor chemistry.

In order to more fully illustrate the nature of the invention and the manner of practicing the same the following examples are presented.

EXAMPLES

Example 1

Continuous esterification of trichlorosilane with methanol to form trimethoxysilane.

To the top spreader tray of a refluxing column (diameter 100 mm., filling depth 3.80 m., 6 × 6 mm. porcelain saddle packing) having a head condenser of 1.2 m² of condensing surface and operating at −48° C, approximately 3.2 kg/h of trichlorosilane and about 2.3 kg/h of anhydrous methanol was fed in liquid form. Temperatures between −20° C and +25° C established themselves at the head of the column, while a boiling temperature of 84° C prevailed in the sump of the column. The sump temperature could be controlled by the correction of the methanol feed (It is lowered by a methanol deficit and it is raised above 84° C by an excess of methanol). Trimethoxysilane (B.P. 84° C) containing approximately 2% dissolved tetramethoxysilane flowed continuously from the sump overflow, and carried an acidity activatable by hydrolysis of less than 20 mg. of hydrogen chloride equivalents per liter.

A single continuous or discontinuous refining distillation yielded absolute trimethoxysilane in a yield of 96.2%. with respect to the trichlorosilane input.

In approximately 720 hours of operation, 2026 kg. of trimethoxysilane was produced in this manner. In addition, about 1120 normal cubic meters of pure hydrogen chloride were obtained (at a rate of about 1.6 Nm³/h) from the head condenser for reuse.

Example 2

Continuous esterification of trichlorosilane with ethanol to form triethoxysilane.

To the top spreader tray of the column described in Example 1, approximately 3.7 kg/h of trichlorosilane and about 3.7 kg/h of anhydrous ethanol were fed continuously in liquid form. Temperatures between about 0° and +28° C establish themseleves at the top of the column, while a boiling temperature of 132.2° C prevailed in the sump of the column. The sump temperature could be controlled by adjusting the ethanol feed (An ethanol deficit reduces it and an excess of ethanol increases it above 132.2° C). Triethoxysilane (B.P. 132.2° C) flowed continuously from the sump overflow, containing approximately 2.6% of dissolved tetraethoxysilane and carrying an acidity activatable by hydrolysis of less than 30 mg. of hydrogen chloride equivalents per liter.

By means of a simple continuous or discontinuous refining distillation, absolute triethoxysilane was obtained in a yield of about 96.7% with respect to the trichlorosilane input.

In approximately 720 hours of operation, 3029 kg. of triethoxysilane was produced in this manner. In addition, about 1260 Nm³ of pure hydrogen chloride (about 1.75 Nm³/h) was obtained through the head condenser for reuse.

Example 3

Continuous esterification of trichlorosilane with 2-methoxyethanol to form tri-2-methoxyethoxysilane.

To the top spreader tray of the column described in Example 1, approximately 2.2 kg/h of a solution of 50 weight percent trichlorosilane in trans-dichlorethylene and approximately 1.86 kg/h of anhydrous 2-methoxyethanol were fed continuously in liquid form. Temperature between +10° and +22° C established themselves at the head of the column, while a boiling temperature of 80.5° C prevailed in the sump of the column. As in Examples 1 and 2, the sump temperature could be controlled by adjusting the feed of the 2-methoxyethanol. An approximately 70% solution of tri-2-methoxyethoxysilane in trans-dichlorethylene flowed continuously from the sump overflow.

Vacuum distillation through a four-tray column, in which the solvent was recovered in reusable form, produced a yield of approximately 94%, with respect to the trichlorosilane input, of absolute tri-2-methoxyethoxysilane having a boiling point of 98° C at 0.2 Torr.

Tetra-2-methoxyethoxysilane of a boiling point of 134° C at 0.2 Torr was formed with a yield of about 4%. Furthermore, hydrogen chloride (approximately 0.5 Nm³/h) was obtained from the head condenser for reuse.

Example 4

Continuous esterification of vinyltrichlorosilane with ethanol to form vinyltriethoxysilane.

To the top spreader tray of the column described in Example 1, approximately 3.6 kg/h of vinyl trichlorosilane and about 3.1 kg/h of anhydrous ethanol were fed continuously in liquid form, while temperatures between +4° and +24° C established themselves in the head of the column and a boiling temperature of 152° C prevailed in the sump. As in Examples 1 to 3, the sump temperature could be controlled by correcting the ethanol feed. Vinyltriethoxysilane (B.P. 152° C) flowed continuously from the sump overflow, carrying an acidity activatable by hydrolysis of less than 30 mg. of hydrogen chloride equivalents per liter, along with less than 0.1% ethanol.

By a single continuous or discontinuous refining distillation, absolute vinyltriethoxysilane was obtained in a yield of about 99% with respect to the vinyltrichlorosilane input.

In addition, about 1.45 Nm³/h of hydrogen chloride was removed by distillation from the head condenser of the synthesis column for reuse.

Example 5

Continuous esterification of tetrachlorosilane with ethanol to form tetraethoxysilane.

To the top spreader tray of the column described in Example 1, about 4.7 kg/h of tetrachlorosilane and about 5.1 kg/h of anhydrous ethanol were fed continuously in liquid form. Temperatures between +18 and +39° C established themselves in the column head and a boiling temperature of 168.9° C prevailed in the sump of the column. As in Examples 1 to 4, the sump temperature could be controlled by varying the ethanol feed. Tetraethoxysilane (B.P. 168.7° C) flowed continuously from the sump overflow, carrying less than 0.1% ethanol and an acidity activatable by hydrolysis of less than 30 mg. of hydrogen chloride equivalents per liter.

Absolute tetraethoxysilane was obtained in a yield of about 98.8% with respect to the tetrachlorosilane input by a single continuous or discontinuous refining distillation.

Also, about 2.5 Nm³/h of hydrogen chloride was removed from the head condenser of the synthesis column for reuse.

In about 7200 hours of operation, 41,200 kilograms of tetraethoxysilane were produced in this manner.

Example 6

Continuous esterification of isobutyltrichlorosilane with methanol to form isobutyldimethoxychlorosilane To the top spreader tray of the column described in Example 1, about 1.6 kg/h of isobutyltrichlorosilane and about 0.54 kg/h of anhydrous methanol were fed continuously in liquid form. Temperatures between −10 and +18° C establish themselves in the head of the column, while a boiling temperature of 156.2° C prevailed in the sump. As in Examples 1 to 5, the sump temperature could be controlled by correcting the methanol feed. Isobutyldimethoxychlorosilane (B.P. 156° C) flowed continuously from the sump overflow and contained isobutyltrimethoxysilane in an amount of 6 to 8%, plus a small amount of isobutylmethoxydichlorosilane.

A single continuous or discontinuous refining distillation gave absolute isobutyldimethoxychlorosilane in a yield of about 90% with respect to the isobutyltrichlorosilane input.

Also, about 0.4 Nm³/h of hydrogen chloride was taken from the head condenser of the synthesis column for reuse.

Example 7

Continuous esterification and trichlorosilane with methanol to form dimethoxychlorosilane.

To the top spreader tray of the column described in Example 1, about 4.7 kg/h of trichlorosilane and about 2.3 kg/h of anhydrous methanol were fed continuously in liquid form. In the head of the column temperatures between −18° and +2° C established themselves, while in the sump a boiling temperature of 70.2° C prevailed. As in Examples 1 to 6, the sump temperature could be controlled by correcting the methanol feed. Dimethoxychlorosilane (B.P. 69.6° C) containing about 4% of trimethyoxysilane and about 1% of methoxydichlorosilane as byproducts flowed continuously from the sump overflow. Absolute dimethoxychlorosilane was obtained from the raw product by a single continuous or discontinuous refining distillation in a yield of about 94% with respect to the trichlorosilane input.

In addition, about 0.8 Nm³/h of hydrogen chloride was obtained from the head condenser of the synthesis column for reuse.

Example 8

Continuous esterification of dimethyldichlorosilane with ethanol to form dimethyldiethoxysilane.

To the top spreader tray of the column described in Example 1, approximately 1.23 kg/h of dimethyldichlorosilane and about 0.87 kg/h of anhydrous ethanol were fed continuously in liquid form. Temperatures between 2° and 29° C established themselves at the top of the column, while at the bottom a boiling temperature of about 115° C prevailed. As in Examples 1 to 7, the sump temperature could be controlled by correcting the rate of the ethanol input. Dimethyldiethoxysilane (B.P. 114.6° C) flowed continuously from the sump overflow, carrying an acidity activated by hydrolysis of less than 30 mg. of hydrogen chloride equivalents per liter.

Absolute dimethyldiethoxysilane was obtained by a single, continuous or discontinuous refining distillation, in a yield of about 99% with respect to the trichlorosilane input.

Also, approximately 0.4 Nm³/h of hydrogen chloride was obtained from the head condenser of the synthesis column for reuse.

What is claimed is:

1. In a process for the preparation of an alkoxysilane of the formula:

$$R_{4-n-m}Si(OR')_nCl_m$$

wherein
R is hydrogen or a saturated or unsaturated, chlorinated or unchlorinated alkyl radical of 1 to 12 carbon atoms;
R' is an alkyl radical of 1 to 11 carbon atoms which can contain a hetero atom in the chain;
m is 0 to 3;
n is 1 to 4;
n + m is equal to or less than 4;
by esterification of a chlorosilane of the formula:

$$R_{4-n}SiCl_n$$

wherein R and n have the previously assigned significance, with an alcohol, the improvement which comprises continuously charging liquid alcohol and liquid chlorosilane simultaneously from separate sources into a distillative reaction zone having a head portion and a sump portion, maintaining the head portion at a temperature sufficient for said esterification, continuously distilling off gaseous HCl formed during said esterification while maintaining the resultant reaction mixture in the sump at its boiling point and continuously separating liquid alkoxy silane from the sump.

2. A process according to claim 1 wherein the temperature of the reaction mixture in the sump is maintained at the boiling point of the desired ester product.

3. A process according to claim 1 wherein a solvent is employed, said solvent is introduced at the head portion of the distillative reaction zone and the temperature of the reaction mixture including solvent in the sump is maintained constantly in the range in which the mixture of the desired silane ester and solvent boils at a constant ratio.

4. A process according to claim 1 wherein the distillation zone comprises a plurality of distillation column trays and the liquid reactants react on the top most column tray.

5. A process according to claim 4 wherein liquid alcohol and liquid chlorosilane react within the upper 15% region of the length of the distillation column.

6. A process according to claim 1 wherein the chlorosilane is selected from the group consisting of trichlorosilane, tetrachlorosilane, methyldichlorosilane, dimethyldichlorosilane, trimethylchorosilane, methyltrichlorosilane, ethyltrichlorosilane, vinyltrichlorosilane, propyltrichlorosilane, allyltrichlorosilane, 3-chloropropyltrichlorosilane, normal butyltrichlorosilane and isobutyltrichlorosilane.

7. A process according to claim 1 wherein said alcohol is selected from the group consisting of methanol, ethanol, propanol, butanol, an octanol, 2-methoxyethanol, 2-ethoxyethanol, 2-methoxyethyldiethyleneglycol ether and tetrahydrofurfuryl alcohol.

* * * * *